United States Patent [19]
Wearne et al.

[11] 3,934,272
[45] Jan. 27, 1976

[54] KNEE PROSTHESIS

[75] Inventors: William Maxwell Wearne; John Edward Harris; Wilfred Potter, all of Melbourne, Australia

[73] Assignee: The University of Melbourne, Melbourne, Australia

[22] Filed: Nov. 19, 1974

[21] Appl. No.: 525,319

[52] U.S. Cl. .................... 3/1.911; 128/92 C
[51] Int. Cl.² ............................. A61F 1/24
[58] Field of Search ................. 3/1.9–1.913, 3/1, 22; 128/92 C

[56] References Cited
UNITED STATES PATENTS

| | | | |
|---|---|---|---|
| 3,698,017 | 10/1972 | Scales et al. | 128/92 C X |
| 3,813,700 | 6/1974 | Tavernetti et al. | 3/1.911 |

FOREIGN PATENTS OR APPLICATIONS

| | | | |
|---|---|---|---|
| 1,122,634 | 5/1956 | France | 128/92 C |

OTHER PUBLICATIONS

"Young Mechanical Knee (No. 6661)", Vitallium Surgical Appliances (catalog), Austenal Co., New York, N.Y., 1964, p. 31.

*Primary Examiner*—Ronald L. Frinks
*Attorney, Agent, or Firm*—Dennison, Dennison, Meserole & Pollack

[57] ABSTRACT

A knee prosthesis comprising upper and lower metal members each having an extension adapted to fit into the marrow cavity of the adjacent femur and tibia the member being interconnected with one member entering the body of the other member in which there are half bearing members, the lower member being capable of rotating about the axis of the body and also, to a predetermined extent about the axis at right angles thereto.

5 Claims, 5 Drawing Figures

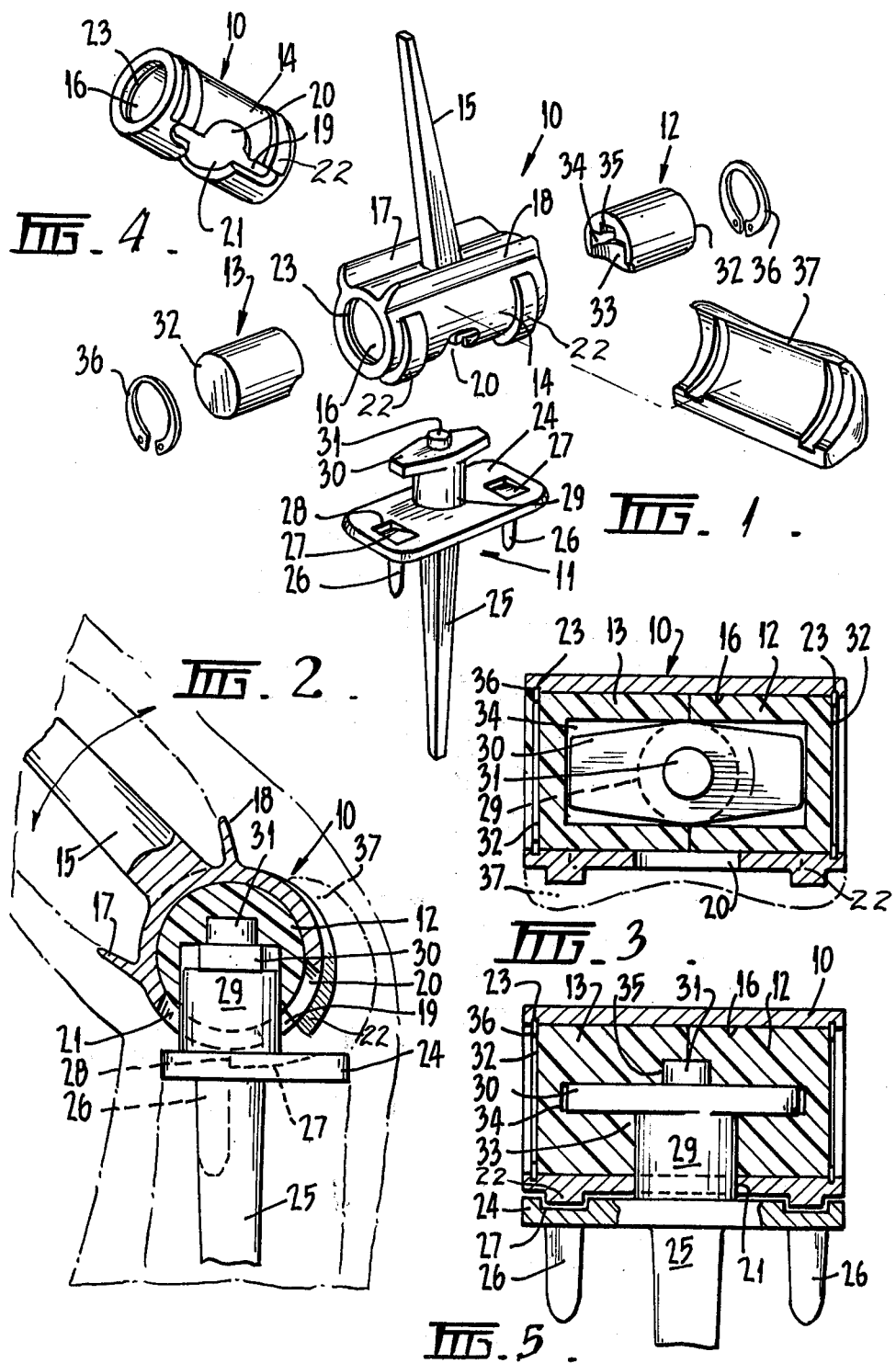

3,934,272

IMPROVED KNEE PROSTHESIS

This invention relates to an improved prosthesis for use in surgical procedures and is particularly applicable to knee prostheses.

Surgical prostheses are well known and there have been previous proposals to provide an effective prosthesis for a knee joint. To date such joints proposed have not been satisfactory as they normally depend on a simple hinging motion which does not permit any rotation of the lower leg about the substantially vertical axis of the prosthesis. During normal walking, for example, these previous prostheses have proved to be unsatisfactory as because of this lack of movement the anchoring rods which enter into the marrow cavity of the femur and tibia have tended to loosen, with consequent disadvantages.

An object of the invention is to provide an improved prosthesis which at least, to a large extent, overcomes the difficulties in previously proposed prostheses.

The invention, in its broadest aspect, comprises a prosthesis having a first member including a rod adapted for connection within the marrow cavity of a femur and a second member having a rod extending therefrom adapted for connection within the marrow cavity of the tibia, the first member having a body of generally hollow cylindrical form and being adapted to receive from each end thereof one of a pair of half bearing members, the second member having an extension adapted to enter the cylindrical portion of the first member and to be received by the half bearing members, the arrangement being such that the second member can rotate about the axis of the cylindrical portion of the first member and can also rotate, to a predetermined extent, about an axis at right angles thereto.

This rotation at right angles to the axis of the cylinder can be provided by forming the half bearing members so that they receive and act as a bearing for portion of the second member extending there between, the bearing members each having a slot adapted to receive one side of a plate extending from the said portion to provide the rotation about an axis substantially at right angles to the cylindrical portion of the first member.

The first and second members are provided with stop means whereby the interconnection between the two members is locked when the rods are in a position corresponding to extension of the leg.

There may also be associated with the members, an element adapted to carry the patella.

In order that the invention may be more readily understood, we shall describe one embodiment of the invention in relation to the accompanying drawings, in which:

FIG. 1 shows the components of the prosthesis in an exploded view;

FIG. 2 shows the prosthesis in a leg in a position between extension and flexion;

FIG. 3 is a partial horizontal section through the prosthesis when assembled;

FIG. 4 is a perspective view of a portion of the upper member showing the engagement of slot;

FIG. 5 is a vertical section through the assembled prothesis;

The two main members, 10,11, of the prosthesis may each be formed from a stainless steel which is acceptable for use with surgical techniques, or can be formed of some other inert acceptable metal. Preferably each component is made of a single piece of metal, preferably by initial casting followed by machining, as it has been found that where screwed joints, or the like are provided within a human body the electro-chemical effect is high and this can cause failure of the components more rapidly than would otherwise be the case.

The bearing halves, 12,13 as will be described hereinafter, are made of a suitable inert plastic material, and we have found that a satisfactory material for this purpose is high density polyethylene. Other suitable plastics could also be used.

The upper component 10, of the prosthesis which is to be connected to the femur, has a body 14, and a rod 15, extending therefrom. The body 14, is substantially cylindrical in form and the rod 15, extends substantially centrally from the cylinder at an angle to a diameter through the cylinder, both relative to the longitudinal axis of the cylinder and also the axis normal thereto. This angle is such as to leave the cylindrical body in the required orientation when the rod is received in the marrow compartment of the femur.

The body 14 has a width and a diameter such as to be received in the area normally occupied by the knee joint and the cylindrical body has a central hollow portion 16.

On the exterior of the body, 14, adjacent to the top thereof, there are a pair of outwardly extending flanges 17,18 which flanges, in side elevation form a portion of a V and which as illustrated, extend fully along the length of the body. If required these flanges may extend only partway along the length of the body.

These flanges, in co-operation with the rod, are adapted to abut the treated lower end of a femur to locate the component relative to the femur.

In the lower surface of the body 14 there is a slot 19 extending a substantial part of the width of the body and parallel to the axis thereof which slot has, in its center, a forwardly extended enlarged portion 20 and extending rearwardly from this enlarged portion and radial of the cylinder and extended slot 21 of the same width as the enlarged portion 20.

Also provided on the periphery of the cylinder on the forward portion thereof and spaced inwardly from the side, are a pair of extensions or stop members 22 which terminate adjacent to the forward edge of the slot 19.

Formed within each end of the cylinder there is a peripheral groove 23, the purpose of which will be described hereinafter.

The lower component 11 of the prosthesis includes a plate 24 having extending downwardly therefrom a rod 25 adapted to be received in the marrow cavity of the tibia. On its lower surface this plate has a pair of downwardly extending pins 26, each spaced from the rod and in its upper surface a pair of broached recesses 27 which are tapered downwardly from the surface of the plate at the forward end thereof and which finish with a shoulder 28 at the rearward end.

Extending upwardly from the plate is a cylindrical bearing surface 29 of substantial diameter, and on the top of this surface, there is a rotation plate 30, which lies in a plane parallel to the main plate and extends outwardly a distance of less than the width of the main plate and a depth less than the depth of the main plate. This rotation plate 30 is slightly tapered from a wider portion at the center to narrower portions at each end.

Above the rotation plate is a further cylindrical bearing 31, which is coaxial with the bearing 29, but of a diameter smaller than that of bearing 29.

The arrangement of the lower component is such that the rotation plate can fit through the slot 19 in the lower surface of the cylindrical member 14 of the upper component and the radius of the enlarged portion 20 of that slot is substantially similar to the radius of the lower cylindrical bearing surface 29. The full arrangement and interengagement will be further described hereinafter.

The prosthesis also consists of the pair of half bearing members 12,13. These members are cylindrical, and are adapted to be a close fit within the central hollow portion 16 of the cylindrical part of the body of the upper component 10. They are of a length such that when they contact in the center of the upper component their outer surfaces 32 terminate adjacent the peripheral grooves 23 in each end of the upper component.

The central portion of the inner end faces of each of these bearing members is formed with three parts. The lower part 33 is relieved to closely abut the lower cylindrical bearing 29 of the second component, the center part 34 comprises a slot sufficiently large to be able to receive the rotation plate 30 and permit a certain degree of rotation of the rotation plate therein as can best been seen from FIG. 3. The upper part 35 is also relieved to receive the upper cylindrical bearing 31.

The components are interengaged as follows:

The lower component 11 is located in the upper component 10 by passing the rotation plate 30 through the slot 19 so that the lower cylindrical bearing surface 29 of the lower component is located in the extended slot 21 and/or the enlarged portion 20 thereof. On this location being achieved, the half bearing members 12,13 are moved into the cylindrical hollow portion 16 of the body in such a way that when they are adjacent at the center of the body they provide bearings for the lower and upper cylindrical bearing surfaces 29,31 of the lower component, and also receive the rotation plate 30.

Once these bearings are located a circlip, 36, which is preferably formed of a plastic of the same type as the bearing, can be placed within each of the peripheral grooves within the cylindrical body, thus locating the half bearings 12,13 in position.

At this time the prosthesis joint is completed and it will be seen that the lower component can rotate around the axis of the cylindrical upper component, the bearing halves remaining stationary relative to the lower component and moving within the hollow cylindrical body of the upper component. The arrangement is such that the components can move relatively rearwardly but when they are approaching the position of extension the extension 22 on the body of the upper component 10 enters the broached recesses 27 in the lower component which correctly aligns the two members and when the two components are in the extension condition, the shoulders of the recesses are struck by the edges of the extension and the bearing member 29 strikes the extended portion 20 of the slide 19 and joint is locked.

At any position other than this not only can the two components rotate about the axis of the cylindrical body of the upper component, but they can also rotate to a certain extent about the axis passing through the two cylindrical bearing portions 31,29 of the lower component. This movement is achieved, as explained before, in that the bearing surfaces are journalled in the half bearings and the degree of movement depends upon the sizes of the slots 34 relative to the size of the rotation plate 30. It is not necessary to provide a great deal of movement in this plane and we believe that movement of the order of 12° would be satisfactory.

We also provide a molding 37, which is preferably of the same plastic as the bearings, and which is adapted to be located between the forward flange 18 of the upper component and the plate 24 of the lower component. This molding has an external shape such as to receive the patella so that when the prosthesis is located and the patella is in position, the appearance of the joint is substantially conventional. This molding 37 also acts as a wiper over the slot 19 and the extensions 20,21 therefrom to prevent the intrusion of tissue into the prosthesis.

In order to fully understand the arrangment of the prosthesis, we shall briefly describe its location in the leg.

The upper and lower components of the prosthesis 10,11 are separated and the upper component is connected to the femur by firstly drilling the marrow compartment centrally so as to receive the rod 15. Before the rod is located however, the lower end of the femur is formed as by the use of a cylindrical saw cutting transverse to the bone to provide a curved undersurface having a diameter equal to the external diameter of the body of the upper component. When this diameter has been formed we use a jig located in the bone to cut away the ends of the bone so that the shape of these ends corresponds to the flanges 17,18 on the upper surface of the component. When the bone has been so treated, the marrow compartment can be filled with a filling material, which may but need not necessarily be an adhesive, and the upper component is located. The location is achieved not only by the rod 15, but also by the upper surface of the body 14 and the flanges 17,18 abutting either side of the bone treated.

The lower component 11 is located in the tibia by drilling the tibia to receive the rod 25 after which we insert a jig by means of which a pair of holes can be formed in the head of the tibia which holes correspond to the pins 26 on the plate 24. Again the marrow cavity is filled with material and the lower component is located. This is located against rotational movement relative to the tibia by the pins 26 entering the holes.

The components are then connected as previously described with the knee joint in flexion and the bearing members 12,13 and the circlips 36 are located. The plastic molding 37 is put into position, the patella located, and the skin re-sewn.

The prosthesis provides a range of movement of the leg substantially equivalent to that which is the case with a natural leg joint, and which locks under extension. The prosthesis we believe, should have a long life, possibly in the order of ten or more years, and will not tend to pull away from the bones as has been the case in previous prostheses. The claims defining the invention are as follows:

We claim:

1. A knee prosthesis including a first member having a rod adapted for connection within the marrow cavity of a femur, a second member having a rod extending therefrom adapted for connection within the marrow cavity of a tibia, said first member having a body of generally hollow cylindrical form, a pair of half bearing members having slots formed therein, each of the bearing members being located in one end of the cylindrical body, the second member having an extension entering the hollow cylindrical body of the first member and received between and located by the half bearing members, the said extension comprising at least one cylindrical bearing portion received between the half bearing members and a plate extending outwardly therefrom which is adapted to enter said slots, the second member being rotatable relative to the first member about the vertical axis of said cylindrical bearing portion, the limits of rotation being controlled by the said plate striking the walls of the slots.

2. A prosthesis as claimed in claim 1 wherein said first member has a longitudinal slot through which said plate can pass and a transverse slot of a width sufficient to receive the said bearing portion, and of a length sufficient to permit the first and second members to move relatively between a position of flexion to one of extension.

3. A prosthesis as claimed in claim 2 wherein at extension the bearing portion strikes the end of the transverse slot to provide a stop.

4. A prosthesis as defined in claim 1 wherein the first member has at least one guide rib extending transverse to the body thereof, the guide rib terminating with a shoulder, and where the second member is provided with co-operating recess means, the guide rib entering the recess means as the prosthesis approaches extension to ensure that on extension the first and second members are locked against rotation.

5. A prosthesis as claimed in claim 1 and further including means on each of said first and second members to locate it against rotation relative to the bone to which it is connected.

* * * * *